(12) United States Patent
Kusunoki et al.

(10) Patent No.: US 9,340,649 B2
(45) Date of Patent: May 17, 2016

(54) METHOD FOR PREPARING A POLYORGANOSILOXANE AND A POLYORGANOSILOXANE

(71) Applicant: SHIN-ETSU CHEMICAL CO., LTD., Tokyo (JP)

(72) Inventors: Takayuki Kusunoki, Annaka (JP); Tsutomu Kashiwagi, Annaka (JP)

(73) Assignee: Shin-Etsu Chemical Co., Ltd., Tokyo (JP)

( * ) Notice: Subject to any disclaimer, the term of this patent is extended or adjusted under 35 U.S.C. 154(b) by 0 days.

(21) Appl. No.: 14/790,549

(22) Filed: Jul. 2, 2015

(65) Prior Publication Data
US 2015/0299397 A1 Oct. 22, 2015

Related U.S. Application Data (62) Division of application No. 14/163,215, filed on Jan. 24, 2014.

(30) Foreign Application Priority Data

Jan. 29, 2013 (JP) ................................. 2013-014750
Dec. 9, 2013 (JP) ................................. 2013-253999

(51) Int. Cl.
C07F 7/18 (2006.01)
C08G 77/04 (2006.01)

(52) U.S. Cl.
CPC ............ C08G 77/045 (2013.01); C07F 7/1808 (2013.01); C07F 7/188 (2013.01)

(58) Field of Classification Search
USPC .................. 556/425, 450, 451, 457
See application file for complete search history.

(56) References Cited

U.S. PATENT DOCUMENTS

| 5,109,093 A | 4/1992 | Rees et al. |
| 5,109,094 A | 4/1992 | Rees et al. |
| 5,204,437 A * | 4/1993 | Ikeno ............... C08L 83/14 525/478 |
| 5,360,858 A | 11/1994 | Fujiki et al. |
| 6,818,721 B2 | 11/2004 | Zha et al. |
| 2009/0088547 A1 | 4/2009 | Schamschurin et al. |

FOREIGN PATENT DOCUMENTS

| JP | 2-235933 A | 9/1990 |
| JP | 3-197486 | 8/1991 |
| JP | 10-106511 A | 4/1998 |
| JP | 11-100550 A | 4/1999 |
| JP | 2006-508216 A | 3/2006 |
| JP | 2010-506982 A | 3/2010 |
| JP | 5-194930 B2 | 5/2013 |

* cited by examiner

*Primary Examiner* — Pancham Bakshi
(74) *Attorney, Agent, or Firm* — Oliff PLC (57) ABSTRACT

A polyorganosiloxane resin represented by the following general formula (5): $(R_3SiO_{1/2})_{l'}(R_2SiO_{2/2})_{m'}(RSiO_{3/2})_{n'}(SiO_{4/2})_{o'}$ (5) wherein R is, independently of each other, a hydrogen atom or a monovalent hydrocarbon group having 1 to 18 carbon atoms, and optionally having an oxygen, halogen, nitrogen or sulfur atom; l', m' and o' are, independently of each other, an integer of from 0 to 10,000; n' is an integer of from 1 to 10,000; a total of l', m' and n' is from 2 to 30,000; and at least one R is a hydrogen atom and at least one R is an —OX group in the molecule, wherein X is an alkyl group having 1 to 10 carbon atoms or an alkoxyalkyl group having 2 to 10 carbon atoms; and at least one hydrogen atom and at least one —OX group bond to one and the same silicon atom.

3 Claims, 3 Drawing Sheets

FIG. 3

METHOD FOR PREPARING A POLYORGANOSILOXANE AND A POLYORGANOSILOXANE

CROSS REFERENCE

This application is a Division of application Ser. No. 14/163,215 filed Jan. 24, 2014, which claims the benefit of Japanese Patent Application No. 2013-014750 filed on Jan. 29, 2013 and Japanese Patent Application No. 2013-253999 filed on Dec. 9, 2013. The disclosure of the prior applications is hereby incorporated by reference in its entirety.

The present invention relates to a method for preparing a polyorganosiloxane, specifically a polyorganosiloxane having one or more hydrosilyl groups, i.e., SiH group and, one or more alkoxysilyl groups, i.e., SiOR group, in a molecule by subjecting one or more organic silicon compounds having a silanol group, i.e., —SiOH, and/or an alkoxysilyl group, i.e., —SiOR, to a condensation reaction with each other. Further, the present invention relates to a polyorganosiloxane thus obtained.

BACKGROUND OF THE INVENTION

Recently, polyorganosiloxanes are attracting attention as a material having good light permeability, good heat resistance, low gas permeability and good chemical stability. Polyorganosiloxanes having various properties are produced by changing types of siloxane monomers, their ratio and reaction conditions in the production process and, accordingly, have been put to practical use in the various fields.

It is known that a polyoraganosiloxane having one or more alkoxysilyl groups and one or more hydrosilyl groups in the molecule has various applications and is very useful as an adhesion improving agent for a silicone elastomer adhesive composition, as described in Japanese Patent Application Laid-Open No. H05-194930, an adhesive component in a primer, as described in Japanese Patent Application Laid-Open No. H11-100550, and an intermediate of a polyorganosiloxane modified with various organic groups, as described in Japanese Patent Application Laid-Open No. H10-106511, as the hydrosilyl group may undergo a hydrosilation and the alkoxyl group may undergo a hydrolytic condensation reaction.

Polyorganosiloxanes are generally prepared by a hydrolysis and condensation reaction of chlorosilane and/or an alkoxysilane in contact with a stoichiometric amount of water in an organic solvent and in the presence of an acid or base catalyst. However, in a case where the polyorganosiloxane having a hydrosilyl group is prepared in this method, the hydrosilyl group is also hydrolyzed. Therefore, this method is not suitable.

Examples of the other general methods for preparing a polyorganosiloxane include a method where an organic silicon compound having a silanol group, i.e., —SiOH, condensation reacts with each other; a method where an organic silicon compound having a silanol group, i.e., —SiOH, condensation reacts with an organic silicon compound having an alkoxysilyl group, i.e., —SiOR; and a method where an organic silicon compound having an alkoxysilyl group, i.e., —SiOR, condensation reacts with each other, wherein R represents an alkyl group or an alkoxyalkyl group. In the aforesaid condensation reactions, an amount of a silanol group remaining in the polyorganosiloxane obtained is small. However, these methods need chemically intense catalysts to cause condensation reaction, such as, for instance, strong acids such as sulfuric acid and hydrochloric acid; strong bases such as sodium hydroxide, potassium hydroxide and tetramethylammonium hydroxide; and Lewis acids. If the aforesaid catalysts are used, a siloxane bond (Si—O—Si) is cut to cause rearrangement during the reaction and, therefore, the polyorganosiloxane obtained has random structures. Further, this method causes hydrolysis of the hydrosilyl group. Further, it is difficult to control the amount of an alkoxysilyl group in the polyorganosiloxane to leave some alkoxysilyl groups in the polyorganosiloxane.

Japanese Patent Application Laid-Open No. H02-235933, Patent Literature 4, describes that a silanol-containing siloxanes is condensated in the presence of sodium or potassium borate or phosphate as a catalyst to prepare an organosilicone condensate. Japanese Patent Application Laid-Open No. H03-197486, Patent Literature 5, describes that a silanol-containing siloxane is condensated in the presence of a catalyst selected from the group consisting of hydroxides, chlorides, oxides and basic metal salts of an alkali metal or an alkaline earth metal to prepare a polyorganosiloxane. Japanese National Phase Publication No. 2006-508216, Patent Literature 6, describes that even hydroxides of magnesium or calcium can work as a catalyst in condition of the presence of a protonic solvent to promote a condensation reaction between a silanol-containing siloxane and an alkoxysilane. Japanese National Phase Publication No. 2010-506982, Patent Literature 7, describes that a silicon-containing compound having a silanol group and/or an alkoxysilyl group reacts in the presence of a catalyst selected from the group consisting of strontium oxide, barium oxide, strontium hydroxide, barium hydroxide and a mixture thereof to prepare an organosilicone condensate.

In the methods described in the afore-mentioned Patent Literatures 4 to 7, rearrangement of the polyorganosiloxane chain is minimized and, thus, a polyorganosiloxane having a controlled structure is obtained. Further, these methods have an advantage that the catalyst is easily separated from the obtained polyorganosiloxane by filtration because these catalysts are solid. These advantages are favorable particularly in fields where accurate control on materials is required and any remaining impurity is untolerable, for instance, the fields of optical materials, electronic materials and medical materials.

PRIOR LITERATURES

Patent Literatures

[Patent Literature 1] Japanese Patent Application Laid-Open No. H05-194930
[Patent Literature 2] Japanese Patent Application Laid-Open No. H11-100550
[Patent Literature 3] Japanese Patent Application Laid-Open No. H10-106511
[Patent Literature 4] Japanese Patent Application Laid-Open No. H02-235933
[Patent Literature 5] Japanese Patent Application Laid-Open No. H03-197486
[Patent Literature 6] Japanese National Phase Publication No. 2006-508216
[Patent Literature 7] Japanese National Phase Publication No. 2010-506982

SUMMARY OF THE INVENTION

As described above, a polyorganosiloxane has useful properties and is used in the various fields. However, in the field of encapsulation of semiconductor devices and sealing, the adhesiveness is low, so that peeling from a subject material occurs often. In order to solve this problem, a hydrogenpolyorganosiloxanes having various substituent groups and reactivities are researched and developed. As stated above, the hydrosilyl group is hydrolyzed to dehydrogenate in the presence of the catalyst such as a strong alkali and, therefore, the synthesis method of the polyorganosiloxane having a hydrosilyl group is limited and a desired polyorganosiloxane has been not obtained yet.

One object of the present invention is to prepare a desired hydrogenpolyoraganosiloxane having an alkoxysilyl group and a hydrosilyl group in the molecule by condensation reacting one or more organic silicon compounds having a silanol group, i.e., —SiOH, and/or an alkoxysilyl group, i.e., —SiOR, with each other.

To solve the aforesaid problems, the present inventors have made research and found that one or more organic silicon compounds having a silanol group, i.e., —SiOH, and/or an alkoxysilyl group, i.e., —SiOX, condensation reacts with each other in the presence of the specific catalyst to effectively give a desired hydrogenpolyorganosiloxane without dehydrogenating a hydrosilyl group during the reaction.

Thus, the present invention is a method for preparing a polyorganosiloxane represented by the following general formula (1):

$$(R_3SiO_{1/2})_l(R_2SiO_{2/2})_m(RSiO_{3/2})_n(SiO_{4/2})_o \qquad (1)$$

wherein R is, independently of each other, a hydrogen atom or a monovalent hydrocarbon group having 1 to 18 carbon atoms, and optionally having an oxygen, halogen, nitrogen or sulfur atom; l, m, n, and o are, independently of each other, an integer of from 0 to 10,000, and a total of l, m and n is from 2 to 30,000; and at least one R is a hydrogen atom and at least one R is an —OX group in the molecule, wherein X is an alkyl group having 1 to 10 carbon atoms or an alkoxyalkyl group having 2 to 10 carbon atoms, wherein the method comprises a step of condensation reacting at least one organic silicon compound having at least one hydrogen atom and at least one —OX' group in the molecule, wherein X' is a hydrogen atom, an alkyl group having 1 to 10 carbon atoms or an alkoxyalkyl group having 2 to 10 carbon atoms, in the presence of a catalyst (D), wherein said catalyst (D) is at least one selected from the group consisting of hydroxides of elements in Group 2 of the periodic table, hydrates of hydroxides of elements in Group 2 of the periodic table, oxides of elements in Group 2 of the periodic table, and hydroxides and oxides of metal elements in Groups 3-15 of the periodic table.

The present method provides an organic silicon compound having one or more hydrosilyl groups, i.e., Si—H, and one or more alkoxysilyl groups, i.e., Si—OX in the molecule, preferably on one and the same silicon atom, wherein X is an alkyl group having 1 to 10 carbon atoms or an alkoxyalkyl group having 2 to 10 carbon atoms.

Further, the present invention provides a novel organic silicon compound obtained in the aforesaid method. The present organic silicon compound is characterized in that at least one hydrogen atom and at least one —OX group bond on one and the same silicon atom.

A first embodiment of the present organic silicon compound is a polyorganosiloxane resin represented by the following general formula (5):

$$(R_3SiO_{1/2})_{l'}(R_2SiO_{2/2})_{m'}(RSiO_{3/2})_{n'}(SiO_{4/2})_{o'} \qquad (5)$$

wherein R is, independently of each other, a hydrogen atom or a monovalent hydrocarbon group having 1 to 18 carbon atoms, and optionally having an oxygen, halogen, nitrogen or sulfur atom; l', m' and o' are, independently of each other, an integer of from 0 to 10,000; n' is an integer of from 1 to 10,000; a total of l', m' and n' is from 2 to 30,000; and at least one R is a hydrogen atom and at least one R is an —OX group in the molecule, wherein X is an alkyl group having 1 to 10 carbon atoms or an alkoxyalkyl group having 2 to 10 carbon atoms; and at least one hydrogen atom and at least one —OX group bond to one and the same silicon atom.

A second embodiment of the present organic silicon compound is a polyorganosiloxane represented by the following formula (6):

wherein $R^1$ is, independently of each other, a monovalent hydrocarbon group having 1 to 18 carbon atoms, and optionally having an oxygen, halogen, nitrogen or sulfur atom; $R^2$ is, independently of each other, a hydrogen atom or $R^1$; $R^3$ is, independently of each other, $R^1$ or an —OX group; X is, independently of each other, an alkyl group having 1 to 10 carbon atoms or an alkoxyalkyl group having 2 to 10 carbon atoms; e is 0 or 1; when e is 0, d is an integer of from 4 to 20 and d' is 0; when e is 1, d is an integer of from 1 to 20 and d' is d; p is an integer of 1 or more; and the siloxane units in the square brackets may form a block structure or a random structure.

A third embodiment of the present organic silicon compound is a polyorganosiloxane represented by the following formula (7):

wherein $R^1$ is, independently of each other, a monovalent hydrocarbon group having 1 to 18 carbon atoms, and optionally having an oxygen, halogen, nitrogen or sulfur atom, $R^2$ is, independently of each other, a hydrogen atom or $R^1$; $R^3$ is, independently of each other, $R^1$ or an —OX group; Q is, independently of each other, $R^1$, an —OX group or a group represented by the following (8):

provided that at least one of Q is the group represented by the aforesaid (8); X is, independently of each other, an alkyl group having 1 to 10 carbon atoms or an alkoxyalkyl group having 2 to 10 carbon atoms; $d^1$ and $d^2$ are, independently of each other, an integer of from 1 to 20; $e^1$ is 1; $e^2$ is 0 or 1; $d^3$ is $d^1$; p and p' are, independently of each other, an integer of 1 or more; and the siloxane units in the square brackets may form a block structure or a random structure.

A fourth embodiment of the present organic silicon compound is a polyorganosiloxane represented by the following formula (9):

wherein $R^1$ is, independently of each other, a monovalent hydrocarbon group having 1 to 18 carbon atoms, and optionally having an oxygen, halogen, nitrogen or sulfur atom; $R^2$ is, independently of each other, a hydrogen atom or $R^1$; $R^3$ is, independently of each other, $R^1$ or an —OX group; $R^5$ is, independently of each other, a hydrogen atom, an alkenyl group having 2 to 10 carbon atoms, or 3-glycidyloxypropyl group, provided that, when at least one $R^3$ bonding to the silicon atom at the end is an —OX group, $R^5$ bonding to this silicon atom is not a hydrogen atom; X is, independently of each other, an alkyl group having 1 to 10 carbon atoms or an alkoxyalkyl group having 2 to 10 carbon atoms; t is 0 or 1; s is an integer of from 1 to 20; when t is 0, s' is 0; when t is 1, s' is s; q is an integer of 1 or more; and the siloxane units in the square brackets may form a block structure or a random structure.

According to the present method, an organic silicon compound having at least one hydrosilyl group and at least one alkoxysilyl group in the molecule is provided. In particular, a hydrogenpolyoraganosiloxane having a hydrogen atom and an alkoxy group on one and the same silicon atom can be provided. The hydrogenpolyoraganosiloxane having a hydrosilyl group and an alkoxysilyl group in the molecule is useful in the field of industry as an adhesion improving agent, a primer and an intermediate of a polyorganosiloxane modified by various organic groups. Further, the present invention provides a polyorganosiloxane having a controlled structure, so that may be used in various fields such as medical or pharmaceutical materials.

DETAILED DESCRIPTION OF THE INVENTION

The present invention will be described below in detail.

The present invention provides a method for preparing a polyorganosiloxane represented by the following formula (1):

$$(R_3SiO_{1/2})_l(R_2SiO_{2/2})_m(RSiO_{3/2})_n(SiO_{4/2})_o \qquad (1)$$

wherein R is, independently of each other, a hydrogen atom or a monovalent hydrocarbon group having 1 to 18 carbon atoms, and optionally having an oxygen, halogen, nitrogen or sulfur atom; l, m, n, and o are, independently of each other, an integer of from 0 to 10,000, and a total of l, m and n is from 2 to 30,000; and at least one R is a hydrogen atom and at least one R is an —OX group in the molecule, wherein X is an alkyl group having 1 to 10 carbon atoms or an alkoxyalkyl group having 2 to 10 carbon atoms.

The aforesaid polyorganosiloxane preferably has at least one silicon atom having at least one hydrogen atom and at least one —OX group on one and the same silicon atom, wherein X is an alkyl group having 1 to 10 carbon atoms or an alkoxyalkyl group having 2 to 10 carbon atoms. The —OX group accounts for preferably 0.2% or more, further preferably 1 to 85%, more preferably 2 to 70%, in number, of R.

The present method will be described below in further detail.

The method for preparing a polyorganosiloxane comprises a step of subjecting one or more organic silicon compounds having at least one —OX' group in the molecule to a condensation reaction in the presence of the specific catalyst (D), wherein X' is a hydrogen atom, an alkyl group having 1 to 10 carbon atoms or an alkoxyalkyl group having 2 to 10 carbon atoms.

The organic silicon compound as the raw material is preferably represented by the following general formula (2):

$$(HR^1{}_aSiO_{(4-a-b)/2}(OX')_b)_n \qquad (2)$$

wherein $R^1$ is, independently of each other, a hydrogen atom or a monovalent hydrocarbon group having 1 to 18 carbon atoms, and optionally having an oxygen, halogen, nitrogen or sulfur atom, X' is as defined above, a and b are independent among the parenthesized repeating units, a is an integer of from 0 to 2 and b is an integer of from 1 to 3, provided that a total of a and b is from 0 to 3, and n is an integer of from 1 to 10,000.

In a first embodiment of the present method, the following (A) and (B1) are reacted in the presence of the specific catalyst (D):
(A) at least one organic silicon compound having at least one silanol group in the molecule and
(B1) at least one organic silicon compound having at least one —OX' group bonded to a silicon atom in the molecule, wherein X' is a hydrogen atom, an alkyl group having 1 to 10 carbon atoms or an alkoxyalkyl group having 2 to 10 carbon atoms, provided that at least one organic silicon compound selected from the group consisting of the components (A) and (B1) has a hydrosilyl group.

In the second embodiment of the present method, the following (B2) is reacted in the presence of the specific catalyst (D):
(B2) one or more organic silicon compounds having at least one —OX group bonded to a silicon atom in the molecule, wherein X is an alkyl group having 1 to 10 carbon atoms or an alkoxyalkyl group having 2 to 10 carbon atoms, provided that at least one organic silicon compound selected from the group consisting of the component (B2) has a hydrosilyl group.

The embodiments will be explained below in detail.

First Embodiment of the Present Method

In the first embodiment of the present method, the component (A) is at least one organic silicon compound having at least one silanol group in the molecule and the component (B1) is at least one organic silicon compound having at least one —OX' group bonded to a silicon atom in the molecule, wherein X' is a hydrogen atom, an alkyl group having 1 to 10 carbon atoms or an alkoxyalkyl group having 2 to 10 carbon atoms. The organic silicon compound may be a monomer, dimer, oligomer or polymer. When the organic silicon compound is an oligomer or a polymer, its structure may be linear, branched or linear with a branched part. Particularly, a linear structure is preferred. In a case where a condensate having a high molecular weight is desired, it is preferred that the polyorganosiloxane has two or more silanol or —OX groups in each molecule. When X' in the component (B1) is a hydrogen atom, the component (A) may be same as the component (B1).

The component (A) may be represented by the following general formula (3):

wherein, $R^1$ is as will be defined below, a and b are independent among the parenthesized repeating units, and a is an integer of from 0 to 3 and b is an integer of from 0 to 4, provided that a total of a and b is from 0 to 4. n is an integer of from 1 to 10,000, preferably 1 to 1,000, provided that the compound (A), organic silicon compound, has at least one —OH group bonded to a silicon atom in the molecule.

The component (B1) may be represented by the following general formula (4):

wherein, $R^1$ and X are as will be defined below, a, b and c are independent among the parenthesized repeating units, and a is an integer of from 0 to 3, b is an integer of from 0 to 4, and c is an integer of from 0 to 3, provided that a total of a, b and c is from 0 to 4. n is an integer of from 1 to 10,000, preferably 1 to 1,000, provided that the compound (B1), organic silicon compound, has at least one —OH group bonded to a silicon atom or —OX group bonded to a silicon atom in the molecule.

In the formulas (3) and (4), $R^1$ is, independently of each other, a hydrogen atom or a monovalent hydrocarbon group having 1 to 18, preferably 1 to 10 carbon atoms, and optionally having an oxygen, halogen, nitrogen or sulfur atom. Examples of $R^1$ include alkyl groups such as methyl, ethyl, propyl, butyl and octyl groups; cycloalkyl groups such as cyclopentyl and cyclohexyl groups; alkenyl groups such as vinyl and allyl groups; aryl groups such as phenyl, tolyl and naphthyl groups; and aralkyl groups such as benzyl, phenylethyl and phenylpropyl groups; and these groups where a part or the whole of their hydrogen atoms bonding to carbon atoms are replaced with a halogen atom(s), such as fluorine, bromine and chlorine atoms, or with a cyano group, such as, for instance, halogen-substituted monovalent hydrocarbon groups such as trifluoropropyl and chloropropyl groups; a cyanoalkyl groups such as a β-cyanoethyl and γ-cyanopropyl groups; 3-methacryloxypropyl group, 3-glycidyloxypropyl group, 3-mercaptopropyl group and 3-aminopropyl group. Among these, methyl group and phenyl are preferred.

In the aforesaid formula (4), X is, independently of each other, an alkyl group having 1 to 10, preferably 1 to 8 carbon atoms or an alkoxyalkyl group having 2 to 10, preferably 2 to 8 carbon atoms. Examples of X include alkyl groups such as methyl, ethyl, propyl, butyl and octyl groups; and alkoxyalkyl group such as methoxymethyl, methoxyethyl and ethoxymethyl groups. Among these, a methyl group is preferred.

As described above, the organic silicon compound represented by the formula (3) or (4) may be a monomer (i.e., n is 1), dimer (i.e., n is 2), oligomers (e.g., n is 3 to 100) or polymer (e.g., n is 100 to 10,000). In particular, a monomer (i.e., n is 1) and a dimer (i.e., n is 2) are preferred.

The component (A) is more preferably an organic silicon compound represented by the following formula (I):

wherein R' is —OH or $R^1$, m is n−1, and $R^1$ and n are as defined above.

Examples of the organic silicon compound represented by the formula (I) includes 1,1,3,3-trimethyldisiloxane-1,3-diol, 1,1,3,3-tetramethyldisiloxane-1,3-diol, 1,1,3,3,5,5-hexamethyltrisiloxane-1,5-diol, 1,1,3,5,5-pentamethyltrisiloxane-1,3,5-triol, 3-glycidyloxypropylmethylsilanetriol, 3-methacryloxypropylsilanetriol, 3-aminopropylsilanetriol, 3-mercaptpropylsilanetriol, 3-chloropropylsilanetriol, silicic acid, phenylsilanediol, phenylmethylsilanediol, diphenylsilanediol, distyrylsilanediol and dipentafluorophenylsilanediol; and an oligomer or a polymer thereof. Among these, diphenylsilanediol is preferred as it is easily available.

The component (B1) is more preferably an organic silicon compound represented by the following formula (II) or (III):

wherein R" is —OH, —OX or $R^1$, preferably —OX or $R^1$, m is n−1, and $R^1$, X and n are as defined above.

wherein R" is —OH, —OX or $R^1$, preferably —OX or $R^1$, at least one R" is —OX, m is n−1, and $R^1$, X and n are as defined above.

Examples of the organic silicon compound represented by the formula (II) include tetramethoxysilane, tetraethoxysilane, trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyltrimethoxymethylsilane, 3-methacryloxypropyltrimethoxysilane, 3-aminopropyltrimethoxysilane, 3-mercaptpropyltrimethoxysilane, 3-chloropropyltrimethoxysilane, methyldimethoxysilane, methyldiethoxysilane, dimethyldimethoxysilane, dimethyldiethoxysilane, phenyldimethoxysilane, phenyldiethoxysilane, phenylmethyldimethoxysilane, diphenyldimethoxysilane, distyryldimethoxysilane, dipentafluorophenyldimethoxysilane, trimethoxysilanol, triethoxysilanol, dimethoxysilanol, diethoxysilanol, methyldimethoxysilanol, decyldimethoxysilanol, vinyldimethoxysilanol, phenyldimethoxysilanol, styryldimethoxysilanol, 3,3,3-trifluoropropyldimethoxysilanol, 3-glicydyloxypropyldimethoxysilanol, 3-methacryloxypropyldimethoxysilanol, 3-aminopropyldimethoxysilanol, 3-mercaptpropyldimethoxysilanol, 3-chloropropyldimethoxysilanol and an oligomer and a polymer of the organic silicon compounds represented by the aforesaid formulas (I) and (II). Tetramethoxysilane and trimethoxysilane are preferred in view of the reactivity.

Examples of the organic silicon compound represented by the formula (III) include dimethoxysilanediol, diethoxysilanediol, methoxysilanediol, ethoxysilanediol, methylmethoxysilanediol, decylmethoxysilanediol, vinylmethoxysilanediol, phenylmethoxysilanediol, styrylmethoxysilanediol, 3,3,3-trifluoropropylmethoxysilanediol, 3-glicydyloxypropylmethoxysilanediol, 3-methacryloxypropylmethoxysilanediol, 3-aminopropylmethoxysilanediol, 3-mercaptpropylmethoxysilanediol, 3-chloropropylmethoxysilanediol and an oligomer and a polymer of the organic silicon compounds represented by the aforesaid formulas (I) to (III).

The raw material monomer which has a hydrosilyl group and is used in the present method for preparing an organic silicon compound having at least one hydrosilyl group and at least one alkoxysilyl group in the molecule is preferably at least one organic silicon compound having a hydrosilyl group selected from the compounds of the formula (II) described above. For instance, trimethoxysilane, triethoxysilane, methyldimethoxysilane and methyldiethoxysilane are preferred.

A blend ratio of the components (A) to (B1) may be decided properly, depending on a desired structure of a product, organic silicon compound. In particular, the number of the —OX group in the component (B1) is larger than the number of the silanol group in the component (A) so as to leave an alkoxysilyl group in the organic silicon compound obtained. Thus, it is preferred that the ratio of the number of the silanol group in the component (A) relative to the number of —OX group in the component (B1) is 0.001 to 0.999, in particular 0.01 to 0.999, further 0.1 to 0.9.

Second Embodiment of the Present Method

In the second embodiment of the present method, the component (B2) is one or more organic silicon compounds having at least one —OX group bonded to a silicon atom in the molecule, wherein X is an alkyl group having 1 to 10 carbon atoms or an alkoxyalkyl group having 2 to 10 carbon atoms. The organic silicon compound may be a monomer, dimer, oligomer and polymer. When the organic silicon compound is an oligomer or a polymer, its structure may be linear, branched or linear with a branched part. Particularly, a linear structure is preferred. In a case where a condensate having a high molecular weight is desired, the polyorganosiloxane preferably has two or more —OX groups in the molecule.

The component (B2) may be represented by the following general formula:

wherein, $R^1$ is, independently of each other, a hydrogen atom or a monovalent hydrocarbon group having 1 to 18, preferably 1 to 10 carbon atoms, and optionally having an oxygen, halogen, nitrogen or sulfur atom. Examples of $R^1$ are as described for the formulas (3) and (4) above. X is, independently of each other, an alkyl group having 1 to 10, preferably 1 to 8 carbon atoms or an alkoxyalkyl group having 2 to 10, preferably 2 to 8 carbon atoms. Examples of X are as described for the formula (4) above.

In the formula, a and c are independent among the parenthesized repeating units, a is an integer of from 0 to 3 and c is an integer of from 0 to 4, provided that a total of a and c is from 0 to 4, provided that the organic silicon compound of formula has at least one —OX group in the molecule.

In the formula, n is an integer of from 1 to 10,000, preferably 1 to 1,000. As described above, the organic silicon compound represented by the formula may be a monomer (i.e., n is 1), dimer (i.e., n is 2), oligomer (e.g., n is 3 to 100) or polymer (e.g., n is 100 to 10,000). In particular, a monomer (i.e., n is 1) and a dimer (i.e., n is 2) are preferred.

The component (B2) is more preferably an organic silicon compound represented by the following formula (IV):

wherein $R'''$ is —OX or $R^1$, m is n−1, and $R^1$, X and n are as defined above.

Examples of the organic silicon compound represented by the aforesaid formula (IV) includes tetramethoxysilane, tetraethoxysilane, trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyldimethoxymethylsilane, 3-methacryloxypropyltrimethoxysilane, 3-aminopropyltrimethoxysilane, 3-mercaptpropyltrimethoxysilane, 3-chloropropyltrimethoxysilane, methyldimethoxysilane, methyldiethoxysilane, dimethyldimethoxysilane, dimethyldiethoxysilane, phenyldimethoxysilane, phenylmethyldimethoxysilane, diphenyldimethoxysilane, distyryldimethoxysilane and dipentafluorophenyldimethoxysilane. Tetramethoxysilane and trimethoxysilane are preferred in view of the reactivity.

The raw material monomer which has a hydrosilyl group and is used in the present method for preparing an organic silicon compound having at least one hydrosilyl group and at least one alkoxysilyl group in the molecule is preferably at least one organic silicon compound having a hydrosilyl group selected from the compounds of the formula (IV) described above. For instance, trimethoxysilane, triethoxysilane, methyldimethoxysilane and methyldiethoxysilane are preferred.

In a case where two or more kinds of the organic silicon compounds are condensation reacted with each other, a mixing ratio of the compounds may be decided properly, depending on a structure of a desired organic silicon compound.

Figure 3:
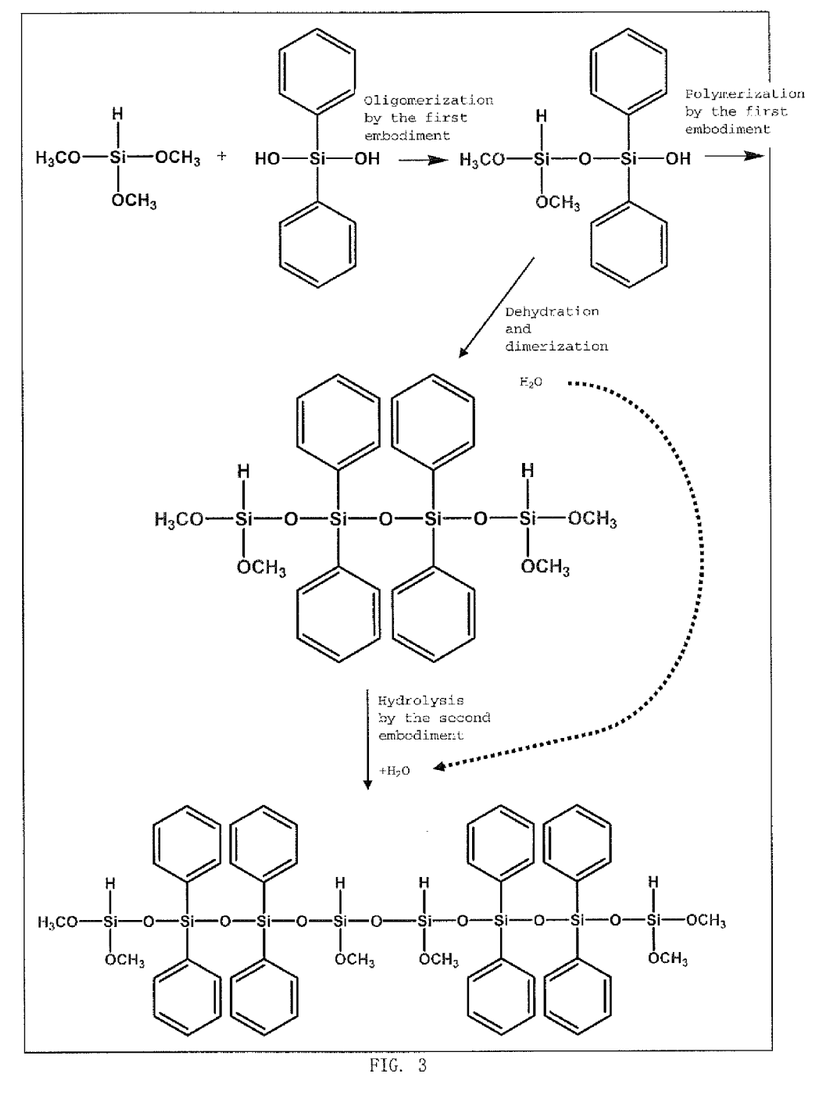
FIG. 3 is a chart indicating a possible reaction mechanism in the present method.

The possible reaction mechanism is shown in the FIG. 3.

The catalyst (D) used in the condensation reaction is at least one selected from the group consisting of hydroxides of elements in Group 2 of the periodic table, hydrates of hydroxides of elements in Group 2 of the periodic table, oxides of elements in Group 2 of the periodic table, and hydroxides or oxides of metal elements in Groups 3-15 of the periodic table (hereinafter, referred to as "metal compound"). The metal compound has a catalytic function for a condensation reaction of an organic silicon compound having a silanol group (—SiOH) and/or an alkoxysilyl group (—SiOX). In view of reactivity or availability, at least one selected from the group consisting of hydroxides of elements in Group 2 of the periodic table, hydrates of hydroxides of elements in Group 2 of the periodic table, oxides of elements in Group 2 of the periodic table, and hydroxides or oxides of elements in Groups 3, 8, 10, 11 and 13 is preferred. Examples of the compound include radium hydroxide, barium hydroxide, strontium hydroxide, calcium hydroxide, magnesium hydroxide, beryllium hydroxide, barium hydroxide octahydrate, barium hydroxide monohydrate, strontium hydroxide octahydrate, barium oxide, strontium oxide, calcium oxide, magnesium oxide, beryllium oxide, lanthanum (III) hydroxide, cerium (IV) hydroxide, zirconium (IV) hydroxide, iron (II) hydroxide, iron (III) hydroxide, cobalt (II) hydroxide, nickel (II) hydroxide, copper (II) hydroxide, gold (III) hydroxide, zinc (II) hydroxide, cadmium (II) hydroxide, aluminum (III) hydroxide, indium (III) hydroxide, thallium (I) hydroxide, lead (II) hydroxide, bismuth (III) hydroxide, manganese (IV) oxide, iron (II) oxide and copper (II) oxide. Among these, barium hydroxide, calcium hydroxide, magnesium hydroxide, strontium hydroxide, lanthanum (III) hydroxide, aluminum (III) hydroxide, iron (II) hydroxide, iron (III) hydroxide and copper (II) hydroxide are preferred in view of availability.

The present method preferably includes a step of surface treating the catalyst (D) with a silane coupling agent (D2) before used in the condensation reaction. On account of the surface treatment of the catalyst, aggregation of the catalyst is prevented and the catalyst is homogeneously dispersed in a reaction solvent, so that the effective surface area as a catalyst is larger. Therefore, the reaction rate is faster and, that is, the catalytic activity is higher.

As the silane coupling agent (D2), any known silane coupling agent may be used. Particularly, in view of the dispersibility of the catalyst, a preferred silane coupling agent has a chemical structure similar to an organic silicon compound which causes a condensation reaction, particularly similar to an organic silicon compound having an alkoxy group. Examples of the silane coupling agent include trimethoxysilane, triethoxysilane, methyltrimethoxysilane, decyltrimethoxysilane, vinyltrimethoxysilane, phenyltrimethoxysilane, styryltrimethoxysilane, 3,3,3-trifluoropropyltrimethoxysilane, 3-glicydyloxypropyldimethoxymethylsilane, 3-glicydyloxypropyltrimethoxysilane, 3-methacryloxypropyltrimethoxysilane, 3-aminopropyltrimethoxysilane, 3-mercaptopropyltrimethoxysilane, 3-chloropropyltrimethoxysilane, 1,1,3,3,5,5-hexamethoxy-1,3,5-trimethyltrisiloxane, 1,1,5,5-tetramethoxy-1,3,5-trimethyltrisiloxane-3-ol, dimethyldimethoxysilane, dimethyldiethoxysilane, phenylmethyldimethoxysilane, diphenyldimethoxysilane, distyryldimethoxysilane, dipentafluorophenyldimethoxysilane and hexamethyldisilazane. Among these, trimethoxysilane, vinyltrimethoxysilane, methyltrimethoxysilane and 3-glicydyloxypropyltrimethoxysilane are preferred.

The surface treatment of the metal compound (D) with the silane coupling agent (D2) may be conducted in a conventional manner. For instance, a wet process and a dry process are utilizable. A mixing ratio of the metal compound (D) to the silane coupling agent (D2) is not limited to particular one. In order not to lose the catalyst activity, the amount of the silane coupling agent (D2) is 0.001 to 100 parts by mass, further preferably 0.01 to 10 parts by mass, per 100 parts by mass of the metal compound (D).

An amount of the catalyst (D) used in the present method, as the amount of the compound before the surface treatment with a silane coupling agent, is 0.0001 to 20 mol %, preferably 0.01 to 10 mol more preferably 0.1 to 5 mol %, relative to a total molar amount of the organic silicone compound to be subjected to a condensation reaction. When the amount of the catalyst (D) is in the afore-mentioned range, a sufficient catalytic effect for the condensation reaction is attained. Further, in a step of removing the catalyst by filtration after the condensation reaction, a desired condensate is recovered effectively without clogging a filter.

The condensation reaction in the present invention may be carried out in the presence of at least one solvent (E). The solvent is used to control a rate and a conversion of the reaction, or used as a diluent for a condensate obtained. The solvent may be one or more selected from non-polar solvents and polar solvents. Examples of the non-polar solvents include hydrocarbons such as n-hexane, n-heptane and isooctane; aromatic hydrocarbons such as toluene and xylene. Examples of the polar solvents include water; alcohols such as methanol, ethanol and isopropanol; alcohol esters; ketones such as acetone, methylethylketone and cyclohexanone; ethers such as diethyl ether and dibutyl ether; esters such as ethyl acetate, isopropyl acetate and butyl acetate; cyano group-substituted hydrocarbons such as acetonitrile; amines; amides such as acetamide; halogenated hydrocarbons such as methylene chloride, chloroform and hexafluoromethaxylene; and sulfur-containing compounds such as dimethylsulfoxide. An amount of the solvent is not limited to particular one. Generally, the amount is such that a concentration of the organic silicon compounds to be subjected to the condensation reaction is 5 to 95 mass %, preferably 20 to 80 mass %. The condensation reaction in the present invention may also be conducted without any solvent.

In the present condensation reaction, any other components may also be added as long as such does not obstruct the progress of the condensation reaction. For instance, a neutral surfactant may be added so as to improve dispersion of a solid catalyst. When the group represented by $R^1$ in the formulas is reactive, a reaction inhibitor may be added. The afore-mentioned components may be used alone or in combination of two or more of them. Further, an amount of the component may be decided properly so that the effects of the present invention are not obstructed.

The condensation reaction in the present invention may be conducted under heating. A temperature is preferably 0 to 150 degrees C., more preferably 60 to 100 degrees C.

The present method preferably further comprises a step of filtering a catalyst after the condensation reaction. In the present method, the catalyst is easily removed from a reaction product in this step. In the filtration, the afore-mentioned solvent (E) may be added in order to control a viscosity of the reaction mixture obtained.

Further, the present method may comprise a step of purification in order to remove an unreacted monomer from the reaction mixture by any known method such as water washing, vacuum strip and treatment with activated carbon.

According to the present method, a hydrogenpolyorganosioxane is provided, which has controlled structure and a desired amount of an alkoxysilyl group and a hydrosilyl group in the molecule.

The present invention further provides a novel organic silicon compound in the aforesaid method. The novel organic silicon compound is characterized in that at least one hydrogen atom and at least one —OX group bond on one and the same silicon atom.

A first embodiment of the present organic silicon compound is a polyorganosiloxane resin represented by the following general formula (5):

$$(R_3SiO_{1/2})_{l'}(R_2SiO_{2/2})_{m'}(RSiO_{3/2})_{n'}(SiO_{4/2})_{o'} \quad (5)$$

wherein R is, independently of each other, a hydrogen atom or a monovalent hydrocarbon group having 1 to 18 carbon atoms, and optionally having an oxygen, halogen, nitrogen or sulfur atom; l', m' and o' are, independently of each other, an integer of from 0 to 10,000; n' is an integer of from 1 to 10,000; a total of l', m' and n' is from 2 to 30,000; and at least one R is a hydrogen atom and at least one R is an —OX group in the molecule, wherein X is an alkyl group having 1 to 10 carbon atoms or an alkoxyalkyl group having 2 to 10 carbon atoms; and at least one hydrogen atom and at least one —OX group bond to one and the same silicon atom. In preferred, 0.2% or more, further preferably 1 to 85%, more preferably 2 to 70%, of R is —OX group.

R is, independently of each other, a hydrogen atom or a monovalent hydrocarbon group having 1 to 18, preferably 1 to 10 carbon atoms, and optionally having an oxygen, halogen, nitrogen or sulfur atom. Examples of R include alkyl groups such as methyl, ethyl, propyl, butyl and octyl groups; cycloalkyl groups such as cyclopentyl and cyclohexyl groups; alkenyl groups such as vinyl and allyl groups; aryl groups such as phenyl, tolyl and naphthyl groups; and aralkyl groups such as benzyl, phenylethyl and phenylpropyl groups; and these groups where a part or the whole of their hydrogen atoms bonding to carbon atoms are replaced with a halogen atom(s), such as fluorine, bromine and chlorine atoms, or with a cyano group, such as, for instance, halogen-substituted monovalent hydrocarbon groups such as trifluoropropyl and chloropropyl groups; a cyanoalkyl groups such as a β-cyano-ethyl and γ-cyanopropyl groups; 3-methacryloxypropyl group, 3-glycidyloxypropyl group, 3-mercaptopropyl group and 3-aminopropyl group. Among these, methyl group and phenyl are preferred.

A second embodiment of the present organic silicon compound is a polyorganosiloxane represented by the following general formula (6):

(6)

wherein $R^1$ is, independently of each other, a monovalent hydrocarbon group having 1 to 18 carbon atoms, and optionally having an oxygen, halogen, nitrogen or sulfur atom; $R^2$ is, independently of each other, a hydrogen atom or $R^1$; $R^3$ is, independently of each other, $R^1$ or an —OX group; X is, independently of each other, an alkyl group having 1 to 10 carbon atoms or an alkoxyalkyl group having 2 to 10 carbon atoms; e is 0 or 1; when e is 0, d is an integer of from 4 to 20 and d' is 0; when e is 1, d is an integer of from 1 to 20 and d' is d; p is an integer of 1 or more; and the siloxane units in the square brackets may form a block structure or a random structure.

A third embodiment of the present organic silicon compound is a polyorganosiloxane represented by the following general formula (7):

(7)

wherein $R^1$ is, independently of each other, a monovalent hydrocarbon group having 1 to 18 carbon atoms, and optionally having an oxygen, halogen, nitrogen or sulfur atom, $R^2$ is, independently of each other, a hydrogen atom or $R^1$; $R^3$ is, independently of each other, $R^1$ or an —OX group; Q is, independently of each other, $R^1$, an —OX group or a group represented by the following (8):

(8)

provided that at least one of Q is the group represented by the aforesaid (8); X is, independently of each other, an alkyl group having 1 to 10 carbon atoms or an alkoxyalkyl group having 2 to 10 carbon atoms; $d^1$ and $d^2$ are, independently of each other, an integer of from 1 to 20; $e^1$ is 1; $e^2$ is 0 or 1; $d^3$ is $d^1$; p and p' are, independently of each other, an integer of 1 or more, preferably 1 to 10, further preferably 1 to 5, in particular preferably both p and p' are 1; and the siloxane units in the square brackets may form a block structure or a random structure.

A fourth embodiment of the present organic silicon compound is a polyorganosiloxane represented by the following general formula (9):

(9)

wherein $R^1$ is, independently of each other, a monovalent hydrocarbon group having 1 to 18 carbon atoms, and optionally having an oxygen, halogen, nitrogen or sulfur atom; $R^2$ is, independently of each other, a hydrogen atom or $R^1$; $R^3$ is, independently of each other, $R^1$ or an —OX group; $R^5$ is, independently of each other, a hydrogen atom, an alkenyl group having 2 to 10 carbon atoms, or 3-glycidyloxypropyl group, provided that, when at least one $R^3$ bonding to the silicon atom at the end is an —OX group, $R^5$ bonding to this silicon atom is not a hydrogen atom; X is, independently of each other, an alkyl group having 1 to 10 carbon atoms or an alkoxyalkyl group having 2 to 10 carbon atoms; t is 0 or 1; s is an integer of from 1 to 20; when t is 0, s' is 0; when t is 1, s' is s; q is an integer of 1 or more, preferably 1 to 10, further preferably 1 to 5, in particular preferably t is 0 and q is 1; and the siloxane units in the square brackets may form a block structure or a random structure.

In the formulas (6) to (9), $R^1$ is, independently of each other, a monovalent hydrocarbon group having 1 to 18, preferably 1 to 12, carbon atoms; and optionally having an oxygen, halogen, nitrogen or sulfur atom. $R^2$ is, independently of each other, a hydrogen atom or $R^1$. $R^3$ is, independently of each other, $R^1$ or a group represented by —OX. Q is, independently of each other, $R^1$, an —OX group, or a group represented by the aforesaid formula (8). Examples of $R^1$ include the same groups as described for the aforesaid formulas (2) to (4). In particular, $R^1$ is a monovalent aromatic hydrocarbon group having 6 to 18, preferably 6 to 12 carbon atoms. The preferred monovalent aromatic hydrocarbon group is phenyl, benzyl, 2-phenylethyl, 2-phenylpropyl, tolyl, xylyl, mesityl, 4-ethylphenyl, naphthyl and biphenyl groups. Among these, phenyl, benzyl, 2-phenylethyl, 2-phenylpropyl and tolyl groups are preferred. In particular, it is preferred that both $R^1$ and $R^2$ are phenyl, benzyl, 2-phenylethyl, 2-phenylpropyl or tolyl group.

In the formulas (6) to (9), X is, independently of each other, an alkyl group having 1 to 10, preferably 1 to 8 carbon atoms or an alkoxyalkyl group having 2 to 10, preferably 2 to 8 carbon atoms. Examples of X include alkyl groups such as methyl, ethyl, propyl, butyl and octyl groups; and alkoxyalkyl group such as methoxymethyl, methoxyethyl and ethoxymethyl groups. Among these, —OX group is preferably a group selected from methoxy, ethoxy, isopropoxy, t-butoxy and phenoxy groups. In particular, a methoxy group is preferred.

In the formula (9), $R^5$ is, independently of each other, a hydrogen atom, alkenyl group having 2 to 10 carbon atoms, or 3-glycidyloxypropyl, provided that when at least one $R^3$ bonding to the silicon atom at the end is an —OX group, $R^5$ bonded to this silicon atom is not a hydrogen atom.

Examples of the compound represented by the formula (6) include the following compounds.

wherein d is an integer of from 4 to 20.

wherein d is an integer of from 4 to 20.

wherein d is an integer of from 4 to 20.

wherein d is an integer of from 1 to 20, d'=d, and p is an integer of 1 or more.

wherein d is an integer of from 1 to 20, d'=d, and p is an integer of 1 or more.

Examples of the compound represented by the formula (7) include the following compound.

wherein

Examples of the compound represented by the formula (9) include the following compound.

The novel organic silicon compound obtained in the present method is characterized in that at least one hydrogen atom and at least one —OX group bond on one and the same silicon atom. The organic silicon compound is useful as an intermediate of various reactive polyorganosiloxanes. Further, the present organic silicon compound is added in a silicone elastomer or applied on a substrate to provide adhesiveness to the silicone elastomer or the substrate. Therefore, the organic silicon compound is useful as an adhesion improving agent.

EXAMPLES

The present invention will be explained below in further detail with reference to a series of the Examples, though the present invention is in no way limited by these Examples. In the following descriptions, the term "part" refers to "part by mass".

The weight average molecular weight (Mw) described in the Examples was determined by a gel permeation chromatography, GPC, and reduced to polystyrene. Conditions in GPC were as follows.

[GPC Conditions]

Solvent: Tetrahydrofuran

Flow rate: 0.6 mL/min.

Columns, all provided by TOSOH Cop.:

TSK Guardcolumn SuperH-L

TSKgel SuperH4000(6.0 mmI.D.×15 cm×1)

TSKgel SuperH3000(6.0 mmI.D.×15 cm×1)

TSKgel SuperH2000(6.0 mmI.D.×15 cm×2)

Column Temperature: 40 degrees C.

Injection Volume: 24 µl of a 0.5% by weight solution in THF.

Detector: Differential refractive index detector (RI)

0.2 g of the product obtained in the Examples was dissolved in 15 g of 1-butanol and, then, 20 g of an aqueous 20 wt % sodium hydroxide solution were added at 25 degrees C. with stirring. The amount of a generated hydrogen gas, $V_H$ [dm$^3$], was applied on the following equation of gas state to obtain an amount of the Si—H group.

Amount of the Si—H group[mol/100 g]=1/{(0.2[g])× 0.0821[atm·dm$^3$·mol$^{-1}$·K$^{-1}$]×(25+273[K])/ (1[atm])×$V_H$[dm$^3$]}

The amount of the alkoxy group, mol/100 g, in the following Example was obtained by determining the $^1$H-NMR spectrum at 400 MHz of the product and calculating an integral value for hydrogen atoms, based on dimethylsulfoxide as an internal standard.

The compounds used in the Examples are as follows.

(1) Diphenylsilanediol (DPS)

(2) 1,1,3,3-Tetramethyldisiloxane-1,3-diol(TDS)

(3) Trimethoxyvinylsilane (TVS)

(4) 3-Glycidyloxypropyltrimethoxysilane (GTS)

(5) Trimethoxysilane (TMS)

(6) Dimethoxymethylsilane (DMS)

(7) Dimethoxydiphenylsilane (DMFS)

(8) Di-o-tolylsilanediol (DTS)

(9) Di-2-phenylethylsilanediol (DPES)

Example 1

216.31 g (1.0 mol) of diphenyl silane diol (DPS), 484.77 g (4.0 mols) of trimethoxysilane (TMS), 200 g of toluene and 60 g of methanol were mixed, and heated to 30 degrees C. with stirring. Then, 0.02 mol of Mg(OH)$_2$ was added to the mixture and heated at 30 degrees C. for 8 hours to react. Mg(OH)$_2$ was removed by filtration, and toluene, methanol and the unreacted TMS were distilled off under a reduced pressure to obtain a polyorganosiloxane mainly comprising a compound represented by the following formula (10):

(10)

Figure 1:
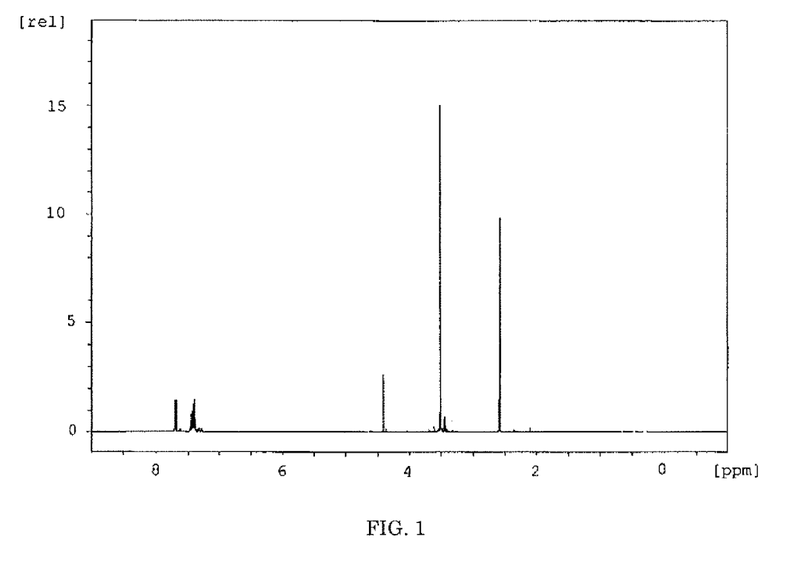
FIG. 1 is a $^1$H-NMR spectrum of the product obtained in Example 1.
Figure 2:
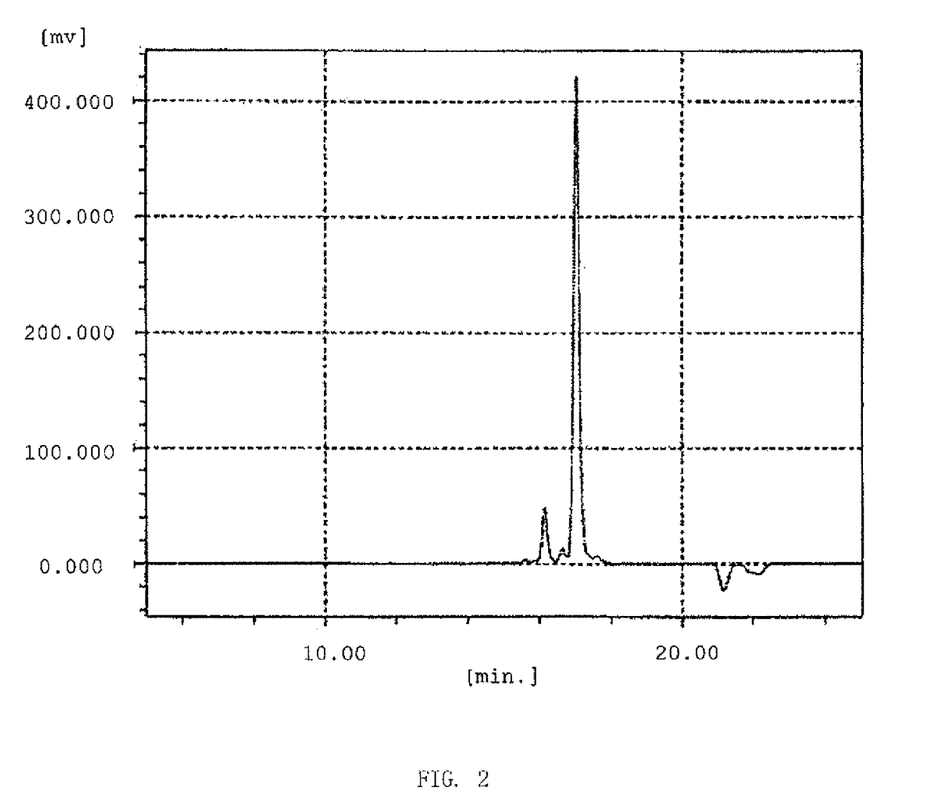
FIG. 2 is a GPC chart of the product obtained in Example 1.

Its Mw was 507, an amount of the Si—H group was 0.50 mol/100 g, and an amount of the alkoxy group was 0.99 mol/100 g. The $^1$H-NMR spectrum and GPC chart of the product obtained are as shown in FIGS. 1 and 2. The ratios of the integration values of the functional groups obtained by analyzing the $^1$H-NMR spectrum are as follows.
—OC$\underline{H}_3$:6.0(3.3 to 3.8 ppm)
—Si$\underline{H}$:1.0(4.3 to 4.6 ppm)
—C$_6\underline{H}_5$:5.1 (7.2 to 8.0 ppm)

Example 2

216.31 g (1.0 mol) of diphenyl silane diol (DPS), 424.80 g (4.0 mots) of dimethoxymethylsilane (DMS), 200 g of toluene and 60 g of methanol were mixed, and heated to 30 degrees C. with stirring. Then, 0.02 mol of Mg(OH)$_2$ was added to the mixture and heated at 30 degrees C. for 16 hours to react. The Mg(OH)$_2$ was removed by filtration, and toluene, methanol and the unreacted DMS were distilled off under a reduced pressure to obtain a polyorganosiloxane mainly comprising a compound represented by the following formula (11):

(11)

Its Mw was 462, an amount of the Si—H group was 0.55 mol/100 g, and an amount of the alkoxy group was 0.55 mol/100 g. The ratios of the integration values of the functional groups obtained by analyzing the $^1$H-NMR spectrum are as follows.
—C$\underline{H}_3$:3.0(−0.3 to 0.3 ppm)
—OC$\underline{H}_3$:3.0(3.3 to 3.8 ppm)
—Si$\underline{H}$:1.0(4.3 to 4.6 ppm)
—C$_6\underline{H}_5$: 5.0(7.2 to 8.0 ppm)

Example 3

259.57 g (1.0 mol) of diphenyl silane diol (DPS), 200 g of toluene and 60 g of tetrahydrofuran were mixed, and heated to 30 degrees C. with stirring. Then, 0.02 mol of Ca(OH)$_2$ was added to the mixture and heated at 30 degrees C. for 16 hours to react. The mixture was cooled to 10 degrees C., 242.38 g (2.0 mols) of trimethoxysilane (TMS) was added thereto and reacted at 10 degrees C. for 8 hours. The Ca(OH)$_2$ was removed by filtration, and toluene, tetrahydrofuran and the unreacted TMS were distilled off under a reduced pressure to obtain a polyorganosiloxane mainly comprising a compound represented by the following formula (12).

(12)

n = 2-4

Its Mw was 916, an amount of the Si—H group was 0.33 mol/100 g, and an amount of the alkoxy group was 0.65 mol/100 g. The ratios of the integration values of the functional groups obtained by analyzing the $^1$H-NMR spectrum are as follows.

—OC$\underline{H}_3$:5.9(3.3 to 3.8 ppm)
—Si$\underline{H}$:1.0(4.3 to 4.6 ppm)
—C$_6\underline{H}_5$:15.2(7.2 to 8.0 ppm)

Example 4

259.57 g (1.2 mols) of diphenyl silane diol (DPS), 104.23 g (0.86 mol) of trimethoxysilane (TMS) and 100 g of toluene were mixed, and heated to 30 degrees C. with stirring. Then, 0.01 mol of Ca(OH)$_2$ was added to the mixture and heated at 30 degrees C. for 4 hours to react. Subsequently, 100 g of toluene were added to the reaction mixture, Ca(OH)$_2$ was removed by filtration, and toluene was distilled off under a reduced pressure to obtain a polyorganosiloxane. Its Mw was 5008, an amount of the Si—H group was 0.33 mol/100 g, and an amount of the alkoxy group was 0.02 mol/100 g. The ratios of the integration values of the functional groups obtained by analyzing the $^1$H-NMR spectrum are as follows.

—OC$\underline{H}_3$:0.18(3.3 to 3.8 ppm)
—Si$\underline{H}$:1.0(4.3 to 4.6 ppm)
—C$_6\underline{H}_5$:14.0(7.2 to 8.0 ppm)

Example 5

166.33 g (1.0 mol) of 1,1,3,3-tetramethyldisiloxane-1,3-diol (TDS), 484.77 g (4.0 mols) of trimethoxysilane (TMS) and 60 g of methanol were mixed, and cooled to 0 degrees C. with stirring. Then, 0.01 mol of Sr(OH)$_2$ was added to the mixture and reacted at 0 degrees C. for 8 hours. Sr(OH)$_2$ was removed by filtration. 10 g of a cation exchange resin, Diaion WK-40, ex. Mitsubishi Chemical Corporation, was added to the mixture, which was shaken for 30 minutes and, then, the cation exchange resin was removed by filtration. Methanol and the unreacted TMS were distilled off under a reduced pressure to obtain a polyorganosiloxane mainly comprising a compound represented by the following formula (13).

(13)

Its Mw was 392, an amount of the Si—H group was 0.57 mol/100 g, and an amount of the alkoxy group was 1.13 mol/100 g. The ratios of the integration values of the functional groups obtained by analyzing the $^1$H-NMR spectrum are as follows.

—C$\underline{H}_3$:6.1(-0.3 to 0.3 ppm)
—OC$\underline{H}_3$:5.95 (3.3 to 3.8 ppm)
—Si$\underline{H}$:1.0(4.3 to 4.6 ppm)

Example 6

240 g of linear dimethylsilicone oil having OH groups at the both terminals, Mw=2400, and 242.38 g (2.0 mols) of trimethoxysilane (TMS) were mixed, and heated to 60 degrees C. with stirring. Then, 0.005 mol of Ba(OH)$_2$ was added to the mixture and reacted at 0 degrees C. for 8 hours. Ba(OH)$_2$ was removed by filtration. 10 g of a cation exchange resin, Diaion WK-40, ex. Mitsubishi Chemical Corporation, was added to the mixture, which was shaken for 30 minutes and, then, the cation exchange resin was removed by filtration. The unreacted TMS was distilled off under a reduced pressure to obtain a polyorganosiloxane. Its Mw was 2695, an amount of the Si—H group was 0.08 mol/100 g, and an amount of the alkoxy group was 0.17 mol/100 g. The ratios of the integration values of the functional groups obtained by analyzing the $^1$H-NMR spectrum are as follows.

—C$\underline{H}_3$:102.2(-0.3 to 0.3 ppm)
—OC$\underline{H}_3$:6.4 (3.3 to 3.8 ppm)
—Si$\underline{H}$:1.0(4.3 to 4.6 ppm)

Example 7

389.36 g (1.5 mols) of diphenyl silane diol (DPS), 118.17 g (0.5 mol) of 3-glycidyloxypropyltrimethoxysilane (GTS) and 400 g of toluene were mixed, and heated to 80 degrees C. with stirring. Then, 1.0 mol of Al(OH)$_3$ was added to the mixture and reacted at 80 degrees C. for 24 hours. After the reaction, the mixture was cooled to 30 degrees C., 363.58 g (3.0 mols) of trimethoxysilane (TMS) and 0.04 mol of Mg(OH)$_2$ were added and, then, reacted at 30 degrees C. for 16 hours. The Al(OH)$_3$ and Mg(OH)$_2$ were removed by filtration, and toluene and the unreacted TMS were distilled off under a reduced pressure to obtain a polyorganosiloxane.

Its Mw was 1175, an amount of the Si—H group was 0.26 mal/100 g, and an amount of the alkoxy group was 0.51 mol/100 g. The ratios of the integration values of the functional groups obtained by analyzing the $^1$H-NMR spectrum are as follows.

—C$_3\underline{H}_6$OC$\underline{H}_2$C$\underline{H}$(O)C$\underline{H}_2$:3-Glycidyloxypropyl group:3.8 (0.3 to 3.3 ppm)
—OC$\underline{H}_3$:5.9(3.3 to 3.8 ppm)
—Si$\underline{H}$:1.0(4.3 to 4.6 ppm)
—C$_6\underline{H}_5$:10.3(7.2 to 8.0 ppm)

Example 8

389.36 g (1.5 mols) of diphenyl silane diol (DPS), 74.12 g (0.5 mol) of vinyltrimethoxysilane (VTS) and 400 g of toluene were mixed, and heated to 80 degrees C. with stirring.

Then, 0.5 mol of Fe(OH)$_3$ was added to the mixture and reacted at 80 degrees C. for 12 hours. After the reaction, the mixture was cooled to 30 degrees C., 484.77 g (4.0 mols) of trimethoxysilane (TMS) and 0.04 mol of Mg(OH)$_2$ were added and, then, reacted at 30 degrees C. for 16 hours. The Fe(OH)$_3$ and Mg(OH)$_2$ were removed by filtration, and toluene and the unreacted TMS were distilled off under a reduced pressure to obtain a polyorganosiloxane. Its Mw was 1090, an amount of the Si—H group was 0.26 mol/100 g, and an amount of the alkoxy group was 0.48 mol/100 g. The ratios of the integration values of the functional groups obtained by analyzing the $^1$H-NMR spectrum are as follows.
—OC$\underline{H}_3$:5.5(3.3 to 3.8 ppm)
—Si$\underline{H}$:1.0(4.3 to 4.6 ppm)
—SiC$\underline{H}$=C$\underline{H}_2$:3.2(5.5 to 6.5 ppm)
—C$_6\underline{H}_5$:10.7(7.2 to 8.0 ppm)

Example 9

49.90 g (0.3 mol) of 1,1,3,3-tetramethyldisiloxane-1,3-diol (TDS) and 15.22 g (0.1 mol) of tetramethoxysilane (TMOS) were mixed, and heated to 80 degrees C. with stirring. Then, 0.01 mol of Mg(OH)$_2$ was added to the mixture and reacted for 8 hours, while distilling off methanol. After the reaction, the mixture was cooled to 30 degrees C., 48.48 g (0.4 mol) of trimethoxysilane (TMS) were added thereto and, then, reacted at 30 degrees C. for 8 hours. The Mg(OH)$_2$ was removed by filtration, and the unreacted TMS was distilled off under a reduced pressure to obtain a polyorganosiloxane. Its Mw was 989, an amount of the Si—H group was 0.24 mol/100 g, and an amount of the alkoxy group was 0.60 mal/100 g. The ratios of the integration values of the functional groups obtained by analyzing the $^1$H-NMR spectrum are as follows.
—C$\underline{H}_3$:14.8(−0.3 to 0.3 ppm)
—OC$\underline{H}_3$:7.5(3.3 to 3.8 ppm)
—Si$\underline{H}$:1.0(4.3 to 4.6 ppm)

Example 10

166.33 g (1.0 mol) of 1,1,3,3-tetramethyldisiloxane-1,3-diol (TDS), 122.05 g (1.05 mols) of dimethylmethoxyvinylsilane (DVS) and 200 g of tetrahydrofuran were mixed, and heated to 30 degrees C. with stirring. Then, 0.02 mol of Ca(OH)$_2$ was added to the mixture and heated at 30 degrees for 8 hours to react. Ca(OH)$_2$ was removed by filtration. 10 g of a cation exchange resin, Diaion WK-40, ex. Mitsubishi Chemical Corporation, was added to the mixture, which was shaken for 30 minutes and, then, the cation exchange resin was removed by filtration. The unreacted DVS were distilled off under a reduced pressure and, then, 242.38 g (2 mols) of trimethoxysilane (TMS) and 0.02 mol of Mg(OH)$_2$ were added thereto and heated at 30 degrees for 8 hours with stirring to react. The Mg(OH)$_2$ was removed by filtration, and the unreacted TMS was distilled off under a reduced pressure to obtain a polyorganosiloxane mainly comprising a compound represented by the following formula (14).

(14)

Its Mw was 412, an amount of the Si—H group was 0.25 mol/100 g, and an amount of the alkoxy group was 0.48 mol/100 g. The ratios of the integration values of the functional groups obtained by analyzing the $^1$H-NMR spectrum are as follows.
—C$\underline{H}_3$:18.1(−0.3 to 0.3 ppm)
—OC$\underline{H}_3$:5.8(3.3 to 3.8 ppm)
—Si$\underline{H}$:1.0(4.3 to 4.6 ppm)
—SiC$\underline{H}$—C$\underline{H}_2$:3.0(5.5 to 6.5 ppm)

Example 11

216.31 g (1.0 mol) of diphenyl silane diol (DPS) and 195.49 g (0.8 mol) of dimethoxydiphenylsilane (DMPS) were mixed, and heated to 80 degrees C. with stirring. Then, 0.02 mol of Ca(OH)$_2$ was added to the mixture and reacted for 16 hours, while distilling off methanol. The mixture was cooled to 10 degrees C., 96.95 g (0.8 mol) of trimethoxysilane (TMS) was added thereto and, then, reacted at 10 degrees C. for 16 hours. The Ca(OH)$_2$ was removed by filtration, and the unreacted TMS was distilled off under a reduced pressure to obtain a polyorganosiloxane mainly comprising a compound represented by the following formula (15).

(15)

n = 7-16

Its Mw was 2521, an amount of the Si—H group was 0.08 mol/100 g, and an amount of the alkoxy group was 0.17 mol/100 g. The ratios of the integration values of the functional groups obtained by analyzing the $^1$H-NMR spectrum are as follows.
—OC$\underline{H}_3$:6.3(3.3 to 3.8 ppm)
—Si$\underline{H}$:1.0(4.3 to 4.6 ppm)
—C$_6\underline{H}_5$:57.2 (7.2 to 8.0 ppm)

Example 12

324.46 g (1.5 mols) of diphenyl silanediol (DPS), 212.4 g (2.0 mols) of dimethoxymethylsilane (DMS) and 100 g of toluene were mixed, and heated to 60 degrees C. with stirring. Then, 0.05 mol of Mg(OH)$_2$ was added to the mixture and reacted at 60 degrees C. for 40 hours. The Mg(OH)$_2$ was removed by filtration, and toluene and the unreacted DMS were distilled off under a reduced pressure to obtain a polyorganosiloxane mainly comprising a compound represented by the following formula (16).

(16)

Its Mw was 811, an amount of the Si—H group was 0.40 mol/100 g, and an amount of the alkoxy group was 0.24 mal/100 g. The ratios of the integration values of the functional groups obtained by analyzing the $^1$H-NMR spectrum are as follows.
—C$\underline{H}_3$:3.0(−0.3 to 0.3 ppm)
—OC$\underline{H}_3$:1.8(3.3 to 3.8 ppm)
—Si$\underline{H}$:1.0(4.3 to 4.6 ppm)
—C$_6\underline{H}_5$:7.1 (7.2 to 8.0 ppm)

Example 13

244.36 g (1.0 mol) of di-o-tolylsilanediol (DTS), 484.77 g (4.0 mols) of trimethoxysilane (TMS), 200 g of toluene and 60 g of methanol were mixed, and heated to 30 degrees C. with stirring. Then, 0.02 mol of Mg(OH)$_2$ was added to the mixture and reacted at 30 degrees C. for 8 hours. The Mg(OH)$_2$ was removed by filtration, and toluene, methanol and the unreacted TMS were distilled off under a reduced pressure to obtain a polyorganosiloxane mainly comprising a compound represented by the following formula (17).

(17)

Its Mw was 540, an amount of the Si—H group was 0.47 mol/100 g, and an amount of the alkoxy group was 0.94 mol/100 g. The ratios of the integration values of the functional groups obtained by analyzing the $^1$H-NMR spectrum are as follows.
—C$_6$H$_4$—C$\underline{H}_3$:3.0(2.0 to 3.0 ppm)
—OC$\underline{H}_3$:6.0(3.3 to 3.8 ppm)
—Si$\underline{H}$:1.0(4.3 to 4.6 ppm)
—C$_6\underline{H}_4$—CH$_3$: 4.1 (7.2 to 8.0 ppm)

Example 14

300.46 g (1.0 mol) of di-2-phenylethylsilanediol (DPES), 484.77 g (4.0 mols) of trimethoxysilane (TMS), 300 g of toluene and 100 g of methanol were mixed, and cooled to 0 degrees C. with stirring. Then, 0.01 mol of Mg(OH)$_2$ was added to the mixture and reacted at 0 degrees C. for 8 hours. The Mg(OH)$_2$ was removed by filtration, and toluene, methanol and the unreacted TMS were distilled off under a reduced pressure to obtain a polyorganosiloxane mainly comprising a compound represented by the following formula (18).

(18)

Its Mw was 540, an amount of the Si—H group was 0.44 mol/100 g, and an amount of the alkoxy group was 0.86 mol/100 g. The ratios of the integration values of the functional groups obtained by analyzing the $^1$H-NMR spectrum are as follows.
—C$\underline{H}_2$C$\underline{H}_2$—C$_6$H$_5$:4.0 (0.3 to 2.5 ppm)
—OC$\underline{H}_3$:6.0 (3.3 to 3.8 ppm)
—Si$\underline{H}$:1.0 (4.3 to 4.6 ppm)
—C$_6\underline{H}_5$:5.0(7.2 to 8.0 ppm)

Example 15

64.89 g (0.3 mol) of diphenylsilanediol (DPS) and 12.72 g (0.105 mol) of trimethoxysilane (TMS) were mixed, and cooled to 0 degrees C. with stirring. Then, 0.5 mol of Mg(OH)$_2$ was added to the mixture, reacted at 0 degrees C. for 4 hours and, then, heated at 60 degrees C. for 4 hours to react. Further, 72.72 g (0.6 mol) of trimethoxysilane (TMS) was added to the reaction mixture and heated at 60 degrees for 8 hours to react. The Mg(OH)$_2$ was removed by filtration, and the unreacted TMS was distilled off under a reduced pressure to obtain a polyorganosiloxane mainly comprising a compound represented by the following formula (19).

Q:

(19)

Its Mw was 1193, an amount of the Si—H group was 0.44 mol/100 g, and an amount of the alkoxy group was 0.62 mol/100 g. The ratios of the integration values of the functional groups obtained by analyzing the $^1$H-NMR spectrum are as follows.

—OC$\underline{H}_3$:4.2(3.3 to 3.8 ppm)
—Si$\underline{H}$:1.0(4.3 to 4.6 ppm)
—C$_6\underline{H}_5$:7.9(7.2 to 8.0 ppm)

As shown in the aforesaid Examples, a polyorganosiloxane having a hydrosilyl group, i.e., —SiH, and an alkoxysilyl group, i.e., —SiOX, in the molecule are prepared by condensation reacting an organic silicon compound having a silanol group, i.e., —SiOH, and/or an alkoxysilyl group, i.e., —SiOX, with each other in the presence of a metal compound catalyst with less dehydrogenation of the hydrosilyl group during the reaction.

INDUSTRIAL APPLICABILITY

According to the present invention, a polyorganosiloxane having a hydrosilyl group, i.e., —SiH, and an alkoxysilyl group, i.e., —SiOX, in the molecule are prepared. The polyorganosiloxane has a hydrosilyl group which may undergo a hydrosilation and an alkoxysilyl group which may undergo a hydrolytic condensation reaction and, therefore, the polyorganosiloxane has various applications and is very useful as an adhesion improving agent for a silicone elastomer adhesive composition, an adhesive component in a primer and an intermediate of a polyorganosiloxane modified with various organic groups.

The invention claimed is:

1. A polyorganosiloxane resin having formula (5):

$(R_3SiO_{1/2})_{l'}(R_2SiO_{2/2})_{m'}(RSiO_{3/2})_{n'}(SiO_{4/2})_{o'}$ (5)

wherein:
R is, independently of each other, a hydrogen atom or a monovalent hydrocarbon group having 1 to 18 carbon atoms, and optionally having an oxygen, halogen, nitrogen or sulfur atom;
l', m' and o' are, independently of each other, an integer of from 0 to 10,000;
n' is an integer of from 1 to 10,000;
a total of l', m' and n' is from 2 to 30,000; and
at least one R is a hydrogen atom and at least one R is an —OX group in the molecule, wherein X is an alkyl group having 1 to 10 carbon atoms or an alkoxyalkyl group having 2 to 10 carbon atoms; and at least one hydrogen atom and at least one —OX group bond to one and the same silicon atom.

2. The polyorganosiloxane resin according to claim 1, wherein the —OX group accounts for 0.2% or more, in number, of R.

3. The polyorganosiloxane according to claim 1, wherein said —OX group is selected from methoxy, ethoxy, isopropoxy, t-butoxy and phenoxy groups.

* * * * *